United States Patent [19]

Lamb et al.

[11] Patent Number: 5,049,377
[45] Date of Patent: Sep. 17, 1991

[54] HAIR-CARE COMPOSITION AND METHODS OF TREATING HAIR

[75] Inventors: Jo Ann Lamb, Midland County; Kathy L. Dillon, Bay County, both of Mich.

[73] Assignee: Dow Corning Corporation, Midland, Mich.

[21] Appl. No.: 487,335

[22] Filed: Mar. 2, 1990

[51] Int. Cl.$^5$ .................... A61K 7/075; A61K 7/08; A61K 7/09; A61K 7/11

[52] U.S. Cl. .......................... 424/70; 424/71; 424/72; 424/78; 424/62; 252/DIG. 13

[58] Field of Search .................. 424/62, 70, 71, 72, 424/78; 514/772; 252/174.15, DIG. 13

[56] References Cited

U.S. PATENT DOCUMENTS

| | | | |
|---|---|---|---|
| 2,891,920 | 6/1959 | Hyde et al. | 528/21 X |
| 3,208,911 | 9/1965 | Oppliger | 428/70 |
| 4,243,657 | 1/1981 | Okumura et al. | 424/47 |
| 4,563,347 | 1/1986 | Starch | 424/70 |
| 4,696,969 | 9/1987 | Thimineur et al. | 524/762 |
| 4,749,732 | 6/1988 | Kohl et al. | 524/43 |
| 4,902,499 | 2/1990 | Bolich, Jr. et al. | 424/70 |
| 4,908,140 | 3/1990 | Bausch et al. | 252/8.8 X |

FOREIGN PATENT DOCUMENTS 2058103  4/1981  United Kingdom .

Primary Examiner—Thurman K. Page
Assistant Examiner—Susan S. Rucker
Attorney, Agent, or Firm—John D. Thallemer

[57] ABSTRACT

Hair care compositions containing a hydrophobic cationic emulsion of a highly branched and crosslinked silicone polymer. The silicone polymer is a polydimethylsiloxane and the silicone emulsions can be formulated into conditioners, styling gels, pump sprays and permanent hair waving products. The compositions are effective in enhancing wet and dry combing and feel of hair.

9 Claims, No Drawings

HAIR-CARE COMPOSITION AND METHODS OF TREATING HAIR

BACKGROUND OF THE INVENTION

The present invention relates to hair care compositions which contain a hydrophobic cationic emulsion of a highly branched and crosslinked silicone polymer, preferably polydimethylsiloxane. These silicone emulsions can be formulated into conditioners, styling gels, pump sprays, permanent hair waving products, and the like and are especially effective in enhancing the wet and dry combing of hair.

It is well known in the art that the incorporation of polydimethylsiloxanes into hair care formulations enhances the manageability, appearance and feel of treated hair. For example, U.S. Pat. No. 4,243,657, issued Jan. 6, 1981, discloses a hair care composition including polydimethylsiloxanes and diol derivatives or branched aliphatic alcohols. Recently, aminoalkyl substituted polydiorganosiloxanes have become popular in hair care formulations. These aminoalkyl substituted polydiorganosiloxane polymers are typically dimethylsiloxane polymers in which some of the methyl groups attached to the polymer chain are replaced by organic groups of amine functionality. Such aminofunctional siloxanes show a stronger affinity for hair surfaces and are not removed as easily as other siloxane polymers. In addition, the aminofunctional siloxanes have been shown to have a greater effect in reducing the average combing force. U.S. Pat. No. 4,563,347, issued Jan. 7, 1986, and U.S. Pat. No. 4,749,732, issued June 7, 1988, teach the use of aminoalkyl substituted polydiorganosiloxanes with other components in hair care compositions to improve combing and feel characteristics. Great Britain Patent No. 2,058,103, (published Apr. 8, 1981), discloses hair conditioning compositions containing a cationic polymer and an oil in water emulsion of an aminofunctional polydimethylsiloxane which improves ease of combing.

In accordance with the present invention, however, it has been discovered that aminoalkyl groups are not necessary to improve the combing and feel characteristics of hair. Instead, the present inventors have found that it is possible to incorporate a hydrophobic cationic emulsion of a highly branched and crosslinked polydimethylsiloxane, hereinafter referred to as the silicone emulsion, into hair care formulations. The degree of crosslinking distinguishes the emulsion of this invention from other emulsions used in the field of cosmetics. For example, U.S. Pat. No. 4,696,969, issued Sept. 29, 1987, discloses an aqueous emulsion composition which can be employed in hair conditioners, which includes a linear polydimethylsiloxane base polymer fluid having a viscosity of up to 100,000 cps. Unlike the prior art, however, the present invention benefits from a crosslinked polydimethylsiloxane. Crosslinking occurs when polyfunctional compounds having more than two functional groups per molecule are used.

A toluene solubility test provides a simple method to distinguish between linear and nonlinear polydimethylsiloxanes because linear siloxanes are soluble in toluene whereas branched and crosslinked siloxanes are not. In addition to differences in solubility, linear and nonlinear polydimethylsiloxanes exhibit different physical properties. Linear polydimethylsiloxanes are liquids which exhibit viscous flow, even at high molecular weights. Branched or crosslinked polydimethylsiloxanes of comparable molecular weight are elastomers. Since the two classes of siloxane polymers have such significant differences in physical properties, it would not be obvious to substitute a highly branched and crosslinked siloxane for a predominantly linear siloxane in hair treatment compositions.

A hydrophobic cationic emulsion of a highly branched and crosslinked silicone polymer for use in fabric care applications to improve rewettability is described in U.S. Pat. No. 4,908,140, issued Mar. 13, 1990, and assigned to the same assignee as the present application. U.S. Pat. No. 4,908,140 discloses a method of enhancing the rewettability of fabrics treated in a laundering operation by contacting the fabrics with a mixture including a rinse cycle fabric softening conditioning composition and a hydrophobic cationic emulsion of a silicone polymer inorder to improve the water absorbing capabilities of fabrics.

However, use of the hydrophobic cationic emulsion in hair care formulations provides advantages neither taught nor appreciated by U.S. Pat. No. 4,908,140. For example, hair care products were not contemplated by U.S. Pat. No. 4,908,140 and hair treated in accordance with the present invention possesses improved wet and dry combing properties which is unrelated to enhancing water absorbency. The hydrophobic silicone emulsion of the present invention effectively sheets the surface of hair making the hair easier to comb and more desirable to feel. Accordingly, the present invention provides compositions and methods of hair treatment possessing significant advantages over the prior art.

SUMMARY OF THE INVENTION

This invention is directed to an aqueous hair care formulation in which the improvement comprises incorporating therein a hydrophobic cationic emulsion of a highly branched and crosslinked silicone polymer, the polymer being an organosiloxane of the formula:

$$R_nSiO_{\frac{4-n}{2}}$$

wherein:

R is selected from the group consisting of hydrogen, a monovalent hydrocarbon radical and a halogenated monovalent hydrocarbon radical; and n is an integer having an average value of from one to less than three, the branched and crosslinked silicone polymer being a highly branched and crosslinked polydimethylsiloxane and including less than about forty percent of linear silicone polymer as determined by extraction with toluene.

This invention is also related to a method for treating hair by incorporating into hair care formulations an effective amount of the hydrophobic cationic emulsion of a highly branched and crosslinked silicone polymer as referred to above.

DETAILED DESCRIPTION OF THE INVENTION

The term "hair" as used in the present invention includes treated and untreated human hair, animal hair, and any type of fiber which requires ease of combing, softness and gloss. The hydrophobic cationic emulsions of highly branched and crosslinked silicone polymers used in the present invention and methods for their preparation are described in U.S. Pat. No. 4,908,140, which is incorporated herein by reference.

The hydrophobic cationic emulsions of the present invention that enhance wet and dry combing in hair care formulations are primarily constituted of highly branched and crosslinked polydimethylsiloxanes and substituted derivatives wherein some methyl groups are substituted with organofunctional groups, i.e. amine, carboxyl, amide. The polydimethylsiloxanes used herein are high molecular weight branched and crosslinked polymers having a molecular weight of at least 100,000 and a viscosity above 50,000 centistokes.

These silicones are formulated into hair care compositions as emulsions. The method of preparation of the emulsions can be any conventional method by which emulsions are typically made. U.S. Pat. No. 2,891,920, issued June 23, 1959, is hereby incorporated by reference as an example of one method of preparing emulsions useable in the present invention. It should be noted that the emulsions prepared using the organofunctional siloxanes of the present invention are oil in water type emulsions. Some water in oil type products are prepared in the initial stages of homogenization during manufacture of the emulsions of this invention but these emulsions soon invert and become oil in water type emulsions. It should be further noted that in some cases where it is desired to optimize the emulsion product, certain co-surfactants may be used in the preparation of the emulsions of this invention. For example, useful co-surfactants are cationic surfactants and nonionic surfactants.

Examples of suitable cationic surfactants include aliphatic amines, aromatic amines with aliphatic substituents, organic quaternary ammonium compounds, polyethylenediamine, polypropanolpolyethanolamines and the like. Preferred cationic surfactants for use in the present invention include ARQUAD® T-27W (N-alkyl trimethyl ammonium chloride), manufactured by Armak, Inc., McCook, Ill. and MIRAPOL® A-15 (polyquaternary ammonium chloride), manufactured by The Miranol Chemical Company, Inc., Dayton, N.J. Examples of suitable nonionic surfactants include condensation products of fatty substances with ethylene oxide, condensation products of phenolic compounds having aliphatic side chains with ethylene oxide and the like. Preferred nonionic surfactants for use in the present invention include MAKON® 10 (alkyphenoxy polyoxyethylene ethanol), available from Stepan Chemical Company, Northfield, Ill., and TERGITOL® 15-S-3 ($C_{11}$-$C_{15}$ secondary alcohol ethoxylate), available from Union Carbide Corp., Danbury, Conn.

The hydrophobic cationic emulsion of this invention is present in hair care formulations in proportions of from 0.05 to 20%, and more preferably from 0.1 to 6%, by weight of the total weight of the composition.

Hair care formulations contemplated herein to benefit from addition of the hydrophobic cationic emulsion of this invention include, but are not limited to, conditioners, styling gels and pump sprays, and may be in the form of aqueous or aqueous-alcoholic dispersions and thickened or unthickened creams, gels, aerosol foams or sprays. In addition, such hair care formulations may contain one or more water soluble quaternised proteins; one or more silicone polymers; conditioning agents; and other adjuvants usually employed in cosmetics, such as sunscreens, perfumes, colorants, preserving agents, sequestering agents, emulsifiers, softeners and foam stabilisers.

The apparatus and testing procedures used herein are as follows:

PREPARATION OF TRESSES

Natural brown, European virgin hair was used. Three hair tresses per treatment were prepared for each material to be tested. About two grams of hair, root end, were glued to a 2" by 2" plastic tab. The tresses were cut so that the length of hair hanging below the tabs was six inches.

BLEACHING/WAVING PROCEDURE

The following solutions and methods of preparation were used in the bleaching and waving of the tresses:

A) Bleaching Solution

The bleaching solution was prepared by mixing seven grams of sodium chloride and 68.0 g of water until the sodium chloride dissolved. To this solution was added 10.0 g of urea, 3.0 g of glycerin and 12.0 g of ammonium hydroxide. The resulting solution was mixed on a 1:1 ratio with 6% hydrogen peroxide.

B) Permanent Waving Solution

The permanent waving solution included a reducing solution and a neutralizing solution. The reducing solution contained 84.4% distilled water, 7.65% concentrated thioglycolic acid and 7.95% concentrated ammonium hydroxide. The pH of the reducing solution was adjusted to 9.5 with sodium hydroxide. The neutralizing solution contained 92.7% distilled water and 7.3% hydrogen peroxide. The pH of the neutralizing solution was adjusted to 3.6 with phosphoric acid.

The bleaching and waving of the tresses was carried out by covering the tresses with the bleaching solution, followed by the reducing solution for twenty minutes each, during which time the tresses were agitated periodically. Each solution was applied only after the previous solution had been removed. The tresses were then rinsed with water before the neutralizing solution was applied. After five minutes, the tresses were again rinsed with water.

SHAMPOO PROCEDURE

Shampoo was prepared according to the following formulation:

| Ingredient | Wt. % |
|---|---|
| Water | 61.95 |
| STANDAPOL ® A[1] | 35.0 |
| MONAMID ® 1159[2] | 3.0 |
| KATHON ® CG[3] | 0.05 |
| | 100.00 |

[1]STANDAPOL ® A (CTFA Adopted Name: Ammonium Lauryl Sulfate), available from Henkel, Inc., Teaneck, NJ., is the ammonium salt of lauryl sulfate where "lauryl" means predominantly a mixture of C12 and C14 alcohols, and is used as a surfactant. The "CTFA Adopted Name" is from the "CTFA Cosmetic Dictionary", 3rd edition, 1982, published by The Cosmetic, Toiletry and Fragrance Association, Inc., Washington, DC.
[2]MONAMID ® 1159 (CTFA Adopted Name: Cocamide DEA), available for Mona Industries, Inc., Paterson, NJ., is N-cocoyldiethanolamide, and is used as a co-surfactant.
[3]KATHON ® CG (CTFA Adopted Name: Methylchloroisothiazolinine (and) Methylisothiozolonone), available from Rohm and Haas Company, Inc., Philadelphia, PA., is a blend of 5-chloro-2-methyl-4-isothiazolin-3-one and 2-methyl-4-isothiazolin-3-one, and is used as a antimicrobial.

This shampoo formulation was prepared by heating water to about 40° C. and adding STANDAPOL ® A and MONAMID ® 1159. This mixture was stirred until a homogenous solution was obtained and KATHON ® CG was added.

The shampooing of the tresses was carried out by rinsing the tresses for 30 seconds, squeezing out the excess water, applying 0.5 grams of shampoo and lathering for one minute, followed by rinsing with water for one minute.

QUANTITATIVE COMBING STUDIES

Comparative quantitative combing studies were performed using an Instron Tensile Testing apparatus available from Instron Corporation, Canton, Mass., which had been adapted with a hard rubber comb. This test involved passing a tress through a comb attached to a strain gauge which in turn is connected to a recording device. Measurements were taken of the peak combing force or maximum force to comb through each tress, as well as of the average combing load (ACL) to comb through each tress. The average combing load was determined by integrating the peak combing force and dividing by the length of hair combed in centimeters and is reported as a relative numerical value. The average combing load is an objective measure of the average force required to comb through a tress.

The invention will be further clarified by a consideration of the following examples. All parts and percentages in the examples are on a weight basis unless otherwise stated.

EXAMPLE 1

This example illustrates the procedure used to prepare the emulsion used in the other examples. A mixture of 52.95 g of water, 8.8 g of ARQUAD ® T-27W, 0.65 g of methyltrimethoxysilane and 35.0 g of cyclomethicone, was prepared. This mixture was passed twice through a Manton-Gaulin 15M8BA homogenizer set at 7500 psig. The resulting emulsion was rendered alkaline by the addition of 0.25 g of a 20% sodium hydroxide solution. The emulsion was then heated at 85° C. for nine hours while being stirred. After cooling to 40° C., 0.15 g of concentrated phosphoric acid and 1.7 g MAKON ® 10 was added while the emulsion continued to be stirred for one hour. The amount of phosphoric acid added should be such that the pH of the emulsion is between 4.5 to 9.0 and preferably from about 6.5 to about 8.0. The pH of these compositions may be adjusted with any cosmetically acceptable alkalizing or acidifying agent. Upon cooling to room temperature 0.5 g of KATHON ® CG was added.

EXAMPLE 2

This example shows that the incorporation of a hydrophobic cationic emulsion of a highly branched and crosslinked silicone polymer into a conditioning formulation enhances the combing and feel of both wet and dry hair that has been treated with such formulations.

| Hair Conditioning Formulation Containing Silicone Emulsion | |
|---|---|
| Ingredient | Wt. % |
| Water | 92.3 |
| Silicone Emulsion | 5.7 |
| CERASYNT ® Q[1] | 1.0 |
| POLAWAX ®[2] | 1.0 |
| | 100.00 |

The above conditioning formulation containing the silicone emulsion was prepared by heating water to about 70° C. and adding CERASYNT ® Q and POLAWAX ®. This mixture was stirred until a homogenous solution was obtained and the silicone emulsion was added.

An organic conditioning formulation equivalent to the conditioning composition described above but without the silicone emulsion, was prepared according to the following formulation:

| Organic Conditioning Formulation | |
|---|---|
| Ingredient | Wt. % |
| Water | 91.0 |
| Stearalkonium Chloride | 5.0 |
| CERASYNT ® Q[1] | 1.0 |
| POLYWAX ®[2] | 1.0 |
| Cetyl Alcohol | 2.0 |
| | 100.00 |

[1]CERASYNT ® Q (CTFA Adopted Name: Glyceryl Stearate SE), available from Van Dyk & Company, Inc., Belleville, NJ., is glyceryl monostearate, and is used as a thickener.
[2]POLAWAX ®, available from Croda, Inc., Newark, NJ., is a nonionic emulsifying wax prepared from higher fatty alcohols and ethylene oxide.

The above comparative organic conditioning formulation was prepared by heating water to about 70° C. and adding CERASYNT ® Q, stearalkonium chloride, POLAWAX ® and cetyl alcohol. The mixture was stirred until a homogenous solution was obtained.

In order to evaluate the conditioning efficacy of the silicone emulsion the tresses were shampooed. The tresses were treated with the conditioner containing the silicone emulsion and with the comparative organic conditioner. Three tresses per treatment were used. Where a conditioner was applied, one gram was massaged into the tress for 60 seconds and the tress was rinsed with water at a temperature of about 40° C. Each wet tress was combed on the Instron Tensile Testing apparatus. Three combing strokes were conducted for each tress and averaged to obtain a representative value. Combs were changed for each treatment. After the average combing load was determined for each wet tress, the tresses were allowed to dry at room temperature for 18 hours before the average combing load was measured on the dry tresses. The test results are summarized in Table I. The higher values indicate hair that was harder to comb.

TABLE I

| Effect of Silicone Emulsion on the Average Combing Load | | |
|---|---|---|
| Treatment | Dry Comb | Wet Comb |
| Conditioner Containing Silicone Emulsion | 9.4 | 24.9 |
| Organic Conditioner (no silicone emulsion) | 17.8 | 32.3 |
| Blank (no conditioning additive) | 29.5 | 58.6 |

Additional evaluations were conducted on the wet and dry tresses and these included subjective combing and feel tests. The subjective evaluations were conducted by a panel of four people. The evaluators rated the tresses on a scale of 1 to 5 with one being the best. The higher values indicate hair that was harder to comb and hair that was more coarse when touched. The average of these results is summarized in Table II.

TABLE II

| Effect of Conditioner Containing Silicone Emulsion on Subjective Combing and Feel | | | | |
|---|---|---|---|---|
| Treatment | Wet Comb | Wet Feel | Dry Comb | Dry Feel |
| Conditioner Containing | 1.33 | 1.42 | 1.25 | 1.33 |

TABLE II-continued

Effect of Conditioner Containing Silicone Emulsion on Subjective Combing and Feel

| Treatment | Wet Comb | Wet Feel | Dry Comb | Dry Feel |
| --- | --- | --- | --- | --- |
| Silicone Emulsion Organic Conditioner (no silicone emulsion) | 2.33 | 2.33 | 2.31 | 2.25 |
| Blank (no conditioning additive) | 2.79 | 2.58 | 2.50 | 2.50 |

As Table I and Table II clearly indicate, the conditioning composition containing the silicone emulsion proved to be superior in terms of ease of combing and desireability of feel than in the cases where the silicone emulsion was not utilized.

EXAMPLE 3

This example shows that a hydrophobic cationic emulsion of a highly branched and crosslinked silicone polymer incorporated into a permanent hair waving formulation enhances the combing and feel of both wet and dry hair that has been treated with such a formulation. In this example, the silicone emulsion was added to the neutralizing solution of a permanent hair waving formulation and was evaluated against a control which was an identical neutralizing solution without the silicone emulsion. The same reducing solution of the permanent hair waving formulation was used for both treatments.

In order to evaluate the effect of the silicone emulsion in a hair waving formulation, tresses were shampooed and immersed in reducing solution. After 20 minutes, the tresses were rinsed with water having a temperature of about 40° C. The tresses were either immersed in the neutralizing solution containing the silicone emulsion or in the neutralizing solution without the silicone emulsion. Three tresses per treatment were used. After five minutes the tresses were rinsed with water. Each wet tress was combed on the Instron Tensile Testing apparatus. Three combing strokes were conducted for each tress and averaged to obtain a representative value. Combs were changed for each treatment. After the average combing load was determined for each wet tress, the tresses were allowed to dry at room temperature for 18 hours before the average combing load was measured on the dry tresses. The test results are summarized in Table III. The higher values, the harder it was to comb the hair.

TABLE III

Effect of Silicone Emulsion in Hair Waving Formulation

| Treatment | Average Combing Load | |
| --- | --- | --- |
| | Dry Comb | Wet Comb |
| Neutralizing Solution Containing Silicone Emulsion | 19.4 | 25.0 |
| Neutralizing Solution without Silicone Emulsion | 27.0 | 70.1 |

As Table III clearly indicates, the permanent hair waving formulation containing the silicone emulsion proved superior in terms of providing ease of combing compared to the waving formulation without the silicone emulsion. In this example, the silicone emulsion was added to the neutralizing solution of the permanent hair waving formulation, however, equivalent results can be obtained by adding the silicone emulsion to the reducing part of the formulation.

EXAMPLE 4

This example shows that a hydrophobic cationic emulsion of a highly branched and crosslinked silicone polymer incorporated into a styling gel enhances the combing and feel of both wet and dry hair that has been treated with such a formulation.

| Styling Gel Formulation | |
| --- | --- |
| Ingredient | Wt. % |
| Water | 85.0 |
| QUATERNIUM ®-15[1] | 0.1 |
| CARBOPOL ® 940[2] | 1.0 |
| Sodium Hydroxide (20% solution) | 1.4 |
| Silicone Emulsion | 2.0 |
| PVP/DMAEM ®[3] | 10.0 |
| Surfactant[4] | 0.5 |
| | 100.00 |

[1] QUATERNIUM ®-15 (CTFA Adopted Name: Quaternium-15), available from Dow Chemical USA, Midland, MI., is cis isomer 1-(3-chloroallyl)-3,5,7-triaza-1-azoniaadamantane chloride, and is used as a antimicrobial.
[2] CARBOPOL ® 940 (CTFA Adopted Name: Carbomer 940), available from B. F. Goodrich Chemical Group, Cleveland, OH., is an acrylic acid polymer crosslinked with a polyfunctional agent, and is used as a thickener.
[3] PVP/DMAEM ® (CTFA Adopted Name: PVP/Dimethylaminoethylmethacrylate Copolymer), available from GAF Corporation, Wayne, NJ., is a copolymer of vinylpyrrolidone and dimethylaminoethylmethacrylate, and is used as a fixative.
[4] Surfactant—is any commercially available mixture of silicone glycol copolymer and polydimethylcyclosiloxane.

The styling gel was prepared by dissolving QUATERNIUM ®-15 into water. CARBOMER ® 940 was added to the water. A solution of sodium hydroxide was added followed by PVP/DMAEM ® and the remaining ingredients. An equivalent styling gel formulation without the silicone emulsion was also prepared.

In order to evaluate the effect of the silicone emulsion in a styling gel formulation, tresses were shampooed. These tresses were then treated with the styling gel which contained the silicone emulsion or with the styling gel without the silicone emulsion. Three tresses per treatment were used. One-half a gram of the respective styling gels was massaged into each tress for 30 seconds. While still wet, subjective combing and feel tests were conducted on the tresses. The tresses were allowed to dry at room temperature for 18 hours before subjective combing and feel tests were conducted on the dry tresses. The subjective evaluations were conducted by a panel of four people. The evaluators rated the tresses on a scale of 1 for the best to 5. The higher values indicate hair that was harder to comb and hair that felt more coarse when touched. The average of these results are summarized in Table IV.

TABLE IV

Effect of Silicone Emulsion in Styling Gel

| | Subjective Evaluations | | | |
| --- | --- | --- | --- | --- |
| Treatment | Wet Comb | Wet Feel | Dry Comb | Dry Feel |
| Styling Gel containing Silicone Emulsion | 2.17 | 2.08 | 1.58 | 1.83 |
| Styling Gel without Silicone Emulsion | 3.33 | 2.92 | 3.08 | 3.17 |

As Table IV clearly indicates, the styling gel containing the silicone emulsion proved to be superior in terms of ease of combing and desireability of feel than the styling gel where the silicone emulsion was not utilized.

EXAMPLE 5

This example shows a hydrophobic cationic emulsion of a highly branched and crosslinked silicone polymer incorporated into a hair styling solution known commercially as a "spritz".

| Hair Spritz Formulation | |
|---|---|
| Ingredient | Wt. % |
| Water | 95.3 |
| Silicone Emulsion | 1.0 |
| Conditioner[1] | 0.5 |
| GAFQUAT ® 734[2] | 1.0 |
| PVP/VA ® E-735[3] | 2.0 |
| GLYDANT ®[4] | 0.2 |
| | 100.00 |

[1]Conditioner—is any commercially available dimethylsiloxane-glycol copolymer.
[2]GAFQUAT ® 734 (CTFA Adopted Name: Polquaternium-11), available from GAF Corporation, Wayne, NJ., is a copolymer of vinyl pyrrolidone and dimethylaminoethylmethacrylate quaternized with dimethyl sulfate, and is used as a conditioning agent.
[3]PVP/VA ® E-735 (CTFA Adopted Name: PVP/VA Copolymer), available from GAF Corporation, Wayne, NJ., is a copolymer of vinylpyrrolidone and vinyl acetate, and is used as a fixative.
[4]GLYDANT ® (CTFA Adopted Name: DMDM Hydantoin), available from Glyco, Inc., Greenwich, CN., is 1-(hydroxymethyl)-5,5-dimethyl hydantoin, and is used as a antimicrobial.

The hair spritz formulation was prepared by combining the water, GAFQUAT ® 734 and PVP/VA ® E-735, then adding the silicone emulsion. The mixture was stirred until a homogenous solution was obtained and GLYDANT ® was added.

Very good combing and feel for both wet and dry hair was obtained after applying this composition to the hair. In addition, this composition remained stable for at least three months at 40° C.

EXAMPLE 6

This example shows a hydrophobic cationic emulsion of a highly branched and crosslinked silicone polymer may be incorporated into a conditioner formulation which also contains a sunscreen.

| Leave-On Conditioning Formulation with Sunscreen | |
|---|---|
| Ingredient | Wt. % |
| Water | 95.95 |
| Silicone Emulsion | 3.0 |
| UVINUL ® MS-40[1] | 1.0 |
| KATHON ® CG[2] | 0.05 |
| | 100.00 |

[1]UVINUL ® MS-40 (CTFA Adopted Name: Benzophenone-4), available from BASF Wyandotte Corporation, Parsippany, NJ., is 2-hydroxy-4-methoxy-benzophen-one-5-sulfonic acid; sulisobenzone, and is used as a UV absorber.
[2]KATHON ® CG (CTFA Adopted Name: Methylchloroisothiazolinone (and) Methylisothiozolinone), available from Rohm and Haas Company Inc., Philadelphia, PA., is a blend of 5-chloro-2-methyl-4-isothiazolin-3-one and 2-methyl-4-isothiazolin-3-one, and is used as a antimicrobial.

The conditioner formulation was prepared by combining the water and UVINUL ® MS-40 and adding the silicone emulsion. The mixture was stirred until a homogenous solution was obtained and KATHON ® CG was added. Very good combing and feel for both wet and dry hair was obtained after applying this composition to the tresses. In addition, this composition remained stable for at least three months at 40° C.

It will be apparent from the foregoing that many other variations and modifications may be made in the structures, compounds, compositions and methods described herein without departing substantially from the essential features and concepts of the present invention. Accordingly, it should be clearly understood that the forms of the invention described herein are exemplary only and are not intended as limitations on the scope of the present invention.

What is claimed is:

1. In a hair treating formulation containing at least one of the materials selected from the group consisting of a conditioning agent, surfactant, neutralizing agent, water soluble quaternised protein, silicone polymer, water, thickener, nonionic emulsifying wax, sunscreen, fixative and antimicrobial, the improvement comprising a conditioning agent which is a hydrophobic cationic aqueous emulsion of a highly branched and crosslinked silicone polymer present in an amount of from 0.05 to 20 percent by weight of the total weight of the composition, the polymer being an organosiloxane of the formula:

$$R_n SiO_{\frac{4-n}{2}}$$

wherein:
R is selected from the group consisting of hydrogen, a monovalent hydrocarbon radical and a halogenated monovalent hydrocarbon radical; and
n is an integer having an average value of from one to less than three, the branched and crosslinked silicone polymer being a highly branched and crosslinked polydimethylsiloxane and including less than about forty percent of linear silicone polymer as determined by extraction with toluene.

2. The formulation of claim 1 wherein the hair care formulation contains from about one half of one percent to about ten percent by weight of the branched and crosslinked silicone polymer emulsion.

3. The formulation of claim 1 wherein the emulsion of the branched and crosslinked silicone polymer contains about thirty-five percent by weight of polymer.

4. A hair conditioner including the emulsion of claim 1 and at least one conditioning agent.

5. A hair waving composition including the emulsion of claim 1 and at least one neutralizing agent.

6. A hair styling solution including the emulsion of claim 1 and at least one fixative.

7. A hair conditioner including the emulsion of claim 1 and at least one sunscreen.

8. A method for treating hair to enhance the wet and dry combing of hair comprising contacting the hair with a hydrophobic cationic aqueous emulsion of a highly branched and crosslinked silicone polymer present in an amount of from 0.05 to 20 percent by weight of the total weight of the composition, the polymer being an organosiloxane of the formula:

$$R_n SiO_{\frac{4-n}{2}}$$

wherein:
R is selected from the group consisting of hydrogen, a monovalent hydrocarbon radical and a halogenated monovalent hydrocarbon radical; and
n is an integer having an average value of from one to less than three, the branched and crosslinked silicone polymer being a highly branched and crosslinked polydimethylsiloxane, and including less than about forty percent of linear silicone polymer as determined by extraction with toluene.

9. The method of claim 8 wherein the emulsion of the branched and crosslinked silicone polymer contains about thirty-five percent by weight of polymer.

* * * * *